United States Patent
Wang et al.

(10) Patent No.: US 12,340,908 B1
(45) Date of Patent: Jun. 24, 2025

(54) REGIONALLY INTEGRATED EMERGENCY STROKE UNIT

(71) Applicant: Beijing Tiantan Hospital, Capital Medical University, Beijing (CN)

(72) Inventors: Yongjun Wang, Beijing (CN); Jing Jing, Beijing (CN); Xuewei Xie, Beijing (CN); Tao Liu, Beijing (CN)

(73) Assignee: Beijing Tiantan Hospital, Capital Medical University, Beijing (CN)

( * ) Notice: Subject to any disclaimer, the term of this patent is extended or adjusted under 35 U.S.C. 154(b) by 0 days.

(21) Appl. No.: 19/069,292

(22) Filed: Mar. 4, 2025

(30) Foreign Application Priority Data

Jul. 24, 2024 (CN) .......................... 202410993951.7

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/0042* (2013.01); *A61B 5/0046* (2013.01);
(Continued)

(58) Field of Classification Search
CPC ........ G16H 50/20; G16H 50/30; G16H 10/20; G16H 10/60; G16H 20/40; G16H 70/20;
(Continued)

(56) References Cited

U.S. PATENT DOCUMENTS

| | | | |
|---|---|---|---|
| 4,915,435 A * | 4/1990 | Levine ................... | A61G 3/001 29/428 |
| 12,059,265 B1 * | 8/2024 | Klein ..................... | G16H 50/30 |

(Continued)

FOREIGN PATENT DOCUMENTS

| | | |
|---|---|---|
| CN | 109637644 A | 4/2019 |
| CN | 115116587 A | 9/2022 |

OTHER PUBLICATIONS

Xiong Jian, "China plan" improves the therapeutic effect of cerebral infarction, Beijing Tiantan Hospital affiliated to Capital Medical University released scientific research results, 2024, vol. 9.

*Primary Examiner* — Fonya M Long
*Assistant Examiner* — Patricia K. Edouard
(74) *Attorney, Agent, or Firm* — Bayramoglu Law Offices LLC

(57) ABSTRACT

A regionally integrated emergency stroke unit includes an information interaction area, an imaging examination area, and a thrombolytic therapy area. A doctor workstation, a comprehensive information surveillance monitor, and a process support artificial intelligence (AI) assistant are set in the information interaction area. A test device, a first television display, a movable low-field magnetic resonance imager, and an AI-assisted decision-making system are set in the imaging examination area. The process support AI assistant performs, via voice interaction or touchscreen keying interaction, automatic inquiry and auxiliary nervous system scale scoring, and further provides real-time retrieval support for a knowledge base and a clinical guideline. The AI-assisted decision-making system is configured to assist in decision-making based on an automatic inquiry result, a scale score result, the test result, and magnetic resonance imaging results of the head and neck, to generate and display a therapy regimen.

7 Claims, 3 Drawing Sheets

(51) Int. Cl.
  *A61B 5/0205*  (2006.01)
  *A61B 5/021*  (2006.01)
  *A61B 5/055*  (2006.01)
  *A61B 5/145*  (2006.01)
  *A61B 5/332*  (2021.01)
  *A61B 50/36*  (2016.01)
  *A61F 17/00*  (2006.01)
  *A61G 3/00*  (2006.01)
  *A61G 10/00*  (2006.01)
  *G06T 7/00*  (2017.01)
  *G16H 10/20*  (2018.01)
  *G16H 10/60*  (2018.01)
  *G16H 20/40*  (2018.01)
  *G16H 50/30*  (2018.01)
  *G16H 70/20*  (2018.01)
  *G16H 70/40*  (2018.01)

(52) U.S. Cl.
  CPC ............ *A61B 5/0205* (2013.01); *A61B 5/021* (2013.01); *A61B 5/055* (2013.01); *A61B 5/14532* (2013.01); *A61B 5/14542* (2013.01); *A61B 5/332* (2021.01); *A61B 5/6801* (2013.01); *A61B 5/742* (2013.01); *A61B 5/749* (2013.01); *A61G 3/001* (2013.01); *G06T 7/0014* (2013.01); *G16H 10/20* (2018.01); *G16H 10/60* (2018.01); *G16H 20/40* (2018.01); *G16H 50/30* (2018.01); *G16H 70/20* (2018.01); *G16H 70/40* (2018.01); *A61B 50/36* (2016.02); *A61B 2560/0493* (2013.01); *A61F 17/00* (2013.01); *A61G 10/00* (2013.01); *G06T 2207/10088* (2013.01); *G06T 2207/20081* (2013.01); *G06T 2207/30016* (2013.01); *G06T 2207/30101* (2013.01)

(58) Field of Classification Search
  CPC ...... G16H 70/40; A61B 5/0046; A61B 5/021; A61B 5/055; A61B 5/14532; A61B 5/14542; A61B 5/332; A61B 5/6801; A61B 5/742; A61B 5/749; A61B 50/36; A61B 2560/0493; A61G 3/001; A61G 10/00; G06T 7/0014; G06T 2207/10088; A61F 17/00
  See application file for complete search history.

(56) References Cited

U.S. PATENT DOCUMENTS

| | | | |
|---|---|---|---|
| 2014/0316821 A1* | 10/2014 | Sheffield | G16B 50/00 705/3 |
| 2015/0019241 A1* | 1/2015 | Bennett | G16H 50/20 705/2 |
| 2017/0262604 A1* | 9/2017 | Francois | G16H 10/60 |
| 2020/0254212 A1* | 8/2020 | Holmes | A61B 5/150076 |
| 2023/0395253 A1* | 12/2023 | Long | G16H 40/67 |

* cited by examiner

| | | | | | |
|---|---|---|---|---|---|
| Upper layer (flip) | Adrenalin hydrochloride 1 mg/1 ml × 5 vials | Isoproterenol 1 mg/ml × 5 vials | Lidocaine 0.1 mg/5 ml × 5 vials | Atropine 1 mg/ml × 5 vials | Dexamethasone 5 mg/ml × 5 vials |
| | Nikethamide 0.375g/1.5 ml × 5 vials | Lobeline 3 mg/1 ml × 5 vials | Dopamine hydrochloride 20 mg/2 ml × 5 vials | Metaraminol 10 mg/1 ml × 5 vials | Deslanoside 0.4 mg/2 ml × 5 vials |
| | Furosemide 20 mg/2 ml × 5 vials | | | | |
| | | | | 50% glucose 10g/20 ml × 3 vials | 50% glucose 10g/20 ml × 2 vials |
| Therapy plate | One management manual of crash truck, one material transfer book of crash truck, one pen, and one temporary record book of medical advices | | | | |
| Inside box | 50% glucose 250 ml × 1 vial<br>0.9% sodium chloride 250 ml × 1 vial<br>Mannitol 250 ml × 1 vial      Infusion pole 1 pole | | | | |
| | 1 ml 2 sets<br>2 ml 2 sets<br>5 ml 2 sets<br>20 ml 2 sets<br>50 ml 1 set | Infusion apparatus 1 PC<br>Sorting bag 1 PC<br>5# scalp acupuncture 2 PCS<br>7# scalp acupuncture 2 PCS<br>9# scalp acupuncture 2 PCS | Gloves 2 sets<br>Cardiac electrode plate 5 PCS<br>Oxygen tube 2 PCS<br>Grinding wheel 1 PC | Flashlight 1 PC<br>Scissors 1 set | Bending tray 1 PC |
| Lower layer | | | Right drawer | Bending tray 1 PC<br>Mouth opener 1 PC<br>Tongue forceps 1 set<br>Tongue depressor 1 PC<br>Sterile gauze 2 PCS | Swab 1 bag<br>Remaining needle 2 PCS<br>Remaining needle application 2 PCS<br>Tourniquet 1 PC<br>Injection plaster 1 bag<br>Adhesive plaster 1 reel<br>Aner Iodine 1 bottle |
| | Mercury sphygmomanometer 1 set<br>Stethoscope 1 PC<br>Wrench 1 PC<br>Breathing bag 1 PC<br>Emergency light 1 PC | | Sputum aspirator 1 set<br>Suction catheter 3 PCS<br>Patch board 1 PC | | |
| Notes: 1. Nurses per shift check and count the items, sign, and timely replenish items that have been used.<br>    2. The trash can on the right side of the rescue truck is nested with a yellow trash bag for use.<br>    3. The bending tray is used to place ampoules and syringe needles. | | | | | |

FIG. 5

REGIONALLY INTEGRATED EMERGENCY STROKE UNIT

CROSS REFERENCE TO RELATED APPLICATION

This patent application claims the benefit and priority of Chinese Patent Application No. 202410993951.7, filed with the China National Intellectual Property Administration on Jul. 24, 2024, the disclosure of which is incorporated by reference herein in its entirety as part of the present application.

TECHNICAL FIELD

The present disclosure relates to the field of medical technologies, and in particular to a regionally integrated emergency stroke unit.

BACKGROUND

About 70% of stroke patients are now known to have an ischemic stroke because of thrombosis or embolism in offending vessels. A large number of studies have shown that when thrombi are lysed or removed early and reperfusion therapy is conducted for brain tissues in an ischemic region, more brain tissues can be salvaged and clinical prognosis is better. However, the proportion of patients who undergo endovascular therapy within 6 hours of an acute ischemic stroke is only 2.17%. In view of this, some scholars provide organized stroke care systems such as building a stroke center and promoting a movable stroke unit, to significantly reduce prehospital and in-hospital delays in stroke patients.

Previous studies have suggested that a hospital admitting stroke patients establishes a stroke unit as much as possible, admits and treats all patients with the acute ischemic stroke in the stroke unit as early as possible, and emphasizes organizational management of the in-hospital delays in the patients with the acute ischemic stroke. However, in the stroke unit, there is a common situation that patients need to travel between consultation rooms, laboratories, imaging rooms, and therapy rooms. This delays valuable therapy time, and there is room for further optimization.

SUMMARY

An objective of the present disclosure is to provide a regionally integrated emergency stroke unit, to concentrate all involved diagnosis and therapy activities in a room after a patient with an acute ischemic stroke arrives at a hospital, thereby significantly shortening a diagnosis time and a therapy time.

To achieve the above objective, the present disclosure provides the following technical solutions.

The present disclosure provides a regionally integrated emergency stroke unit, including: an information interaction area, an imaging examination area, and a thrombolytic therapy area, where a doctor workstation, a comprehensive information surveillance monitor, and a process support AI (artificial intelligence) assistant are set in the information interaction area; the doctor workstation includes a computer, a file rack, and a folding table; the computer is configured for a doctor to enter information; the file rack is configured to place a document; the folding table is configured to temporarily place and store a medical device and a document; the comprehensive information surveillance monitor is configured to display basic information, an arrival time at a hospital, an arrival time at a clinic, and vital signs of a patient; and the process support AI assistant is configured to perform, via voice interaction or touchscreen keying interaction, automatic inquiry and auxiliary nervous system scale scoring, and further provide real-time retrieval support for a knowledge base and a clinical guideline;

a test device, a first television display, a movable low-field magnetic resonance imager, and an AI-assisted decision-making system are set in the imaging examination area; the test device is configured to perform electrocardiogram examination and pharmacogenetic testing, and monitor oxygen saturation, a blood pressure, and peripheral blood glucose of the patient, to obtain a test result; the first television display is configured to amplify content on the comprehensive information surveillance monitor for display; the movable low-field magnetic resonance imager is configured to perform magnetic resonance imaging (MRI) on a head and neck of the patient; the AI-assisted decision-making system is in communication connection with the comprehensive information surveillance monitor, the process support AI assistant, the test device, the first television display, and the movable low-field magnetic resonance imager separately; and the AI-assisted decision-making system is configured to assist in decision-making based on an automatic inquiry result, a scale score result, the test result, and MRI results of the head and neck, to generate and display a therapy regimen; and a small refrigerator, a first aid medicine cabinet, and a storage cabinet are set in the thrombolytic therapy area, and configured to store medicines, reagents, and first aid medicines with different temperature requirements; an ambulance and a vital signs monitoring system are further set in the thrombolytic therapy area; the ambulance is configured to rescue the patient in medical emergency; and the vital signs monitoring system is configured to monitor and display the vital signs of the patient in real time.

Optionally, an intelligent interaction module is disposed in the process support AI assistant; and the intelligent interaction module is configured to perform, based on an emergency structured record, structured questioning on key medical information about the patient such as a time of onset, an onset symptom, a concomitant symptom, a past medical history, and an allergy history, perform voice recognition on an answer of the patient and/or a family of the patient, and perform structured entry of the key medical information.

Optionally, the intelligent interaction module is further configured to score via voice interaction or touchscreen keying interaction with the patient and/or the family of the patient based on the auxiliary nervous system scale including a National Institute of Health stroke scale (NIHSS), an age, blood pressure, clinical features, duration, diabetes (ABCD2) scale, and a pre-morbid modified rankin scale (mRS), to obtain the scale score result.

Optionally, a large language model is further stored in the intelligent interaction module; the large language model includes a knowledge base related to clinical diagnosis and therapy of a stroke, including a clinical scale, a guideline for acute cerebral infarction, a guideline for secondary prevention of cerebral infarction, a guideline for diagnosis and therapy of cerebral hemorrhage, a guideline for clinical diagnosis and therapy of subarachnoid hemorrhage; and in a process of diagnosis and therapy, retrieval of the knowledge base and the clinical guideline is implemented via voice interaction or touchscreen keying interaction with the doctor.

Optionally, the intelligent interaction module is further configured to provide, via voice interaction or touchscreen keying interaction with the patient and/or the family of the patient, functions of explaining a medical process, illuminating a therapy regimen, and signing an informed consent form.

Optionally, the test device includes an electrocardiogrameable electrocardiogram monitor, a fingertip pulse oximeter, a sphygmomanometer, a glucometer, and a non-invasive rapid genotyping tester.

Optionally, a movable MRI system is integrated inside the movable low-field magnetic resonance imager; and the movable MRI system implements, based on low-field and high-field MRI datasets of the patient, image super-resolution reconstruction through an image reconstruction method based on deep learning, to obtain the MRI results of the head and neck.

Optionally, the AI-assisted decision-making system is configured to recognize a site of acute cerebral infarction from the MRI results of the head and neck through a deep learning method, and automatically calculate an infarct volume; the AI-assisted decision-making system is further configured to determine, based on a magnetic resonance angiography (MRA) sequence of movable magnetic resonance, whether the patient exhibits intracranial large artery occlusion/stenosis; and the AI-assisted decision-making system is further configured to align a different sequence to standard space using an automatic alignment technique, to implement automatic recognition on a diffusion-weighted imaging-fluid attenuated inversion recovery (DWI/FLAIR) mismatch of the site of acute cerebral infarction, determine an approximate time of onset of wake-up stroke, and guide reperfusion therapy.

Optionally, the AI-assisted decision-making system is further configured to determine, based on image interpretation information and the scale score result, whether the patient has a clinical-imaging mismatch, and assist, in combination with the infarct volume, in determining whether endovascular therapy needs to be conducted for the patient to implement intracranial reperfusion.

Optionally, a second television display and a trash can are further set in the thrombolytic therapy area; the second television display is configured to display content on the comprehensive information surveillance monitor; and the trash can is configured to temporarily place medical garbage or household garbage.

According to specific embodiments provided in the present disclosure, the present disclosure has the following technical effects:

The present disclosure provides the regionally integrated emergency stroke unit by sorting out a consultation process of an acute ischemic stroke, to integrate the information interaction area, the imaging examination area, and the thrombolytic therapy area into a consultation room. In other words, all involved diagnosis and therapy activities are concentrated in a room after a patient with an acute ischemic stroke arrives at a hospital, and a consultation room, an examination room, and a thrombolysis room for the patient with an ischemic stroke are integrated and systematically managed in an organized manner. Therefore, a one-stop solution can be applied to therapy of the acute ischemic stroke. This resolved a problem that a time from arrival to therapy of the patient is significantly prolonged because of triage, inquiry, physical examination, and laboratory tests scattered in different departments of the emergency and many disciplines involved in diagnosis and therapy after the patient arrives at the hospital. Therefore, the consultation and therapy time of the patient is significantly shortened.

BRIEF DESCRIPTION OF THE DRAWINGS

To describe the technical solutions in embodiments of the present disclosure or in the prior art more clearly, the accompanying drawings required for the embodiments are briefly described below. Apparently, the accompanying drawings in the following description show merely some embodiments of the present disclosure, and those of ordinary skill in the art may still derive other accompanying drawings from these accompanying drawings without creative efforts.

FIG. 5 is a list of items stored in a small ambulance.

DETAILED DESCRIPTION OF THE EMBODIMENTS

The technical solutions of the embodiments of the present disclosure are clearly and completely described below with reference to the drawings in the embodiments of the present disclosure. Apparently, the described embodiments are merely a part rather than all of the embodiments of the present disclosure. All other embodiments obtained by a person of ordinary skill in the art based on the embodiments of the present disclosure without creative efforts shall fall within the protection scope of the present disclosure.

An objective of the present disclosure is to provide a regionally integrated emergency stroke unit, to concentrate all involved diagnosis and therapy activities in a room after a patient with an acute ischemic stroke arrives at a hospital, thereby significantly shortening a diagnosis time and a therapy time.

In order to make the above objective, features and advantages of the present disclosure clearer and more comprehensible, the present disclosure will be further described in detail below in combination with accompanying drawings and particular implementation modes.

Figure 1:
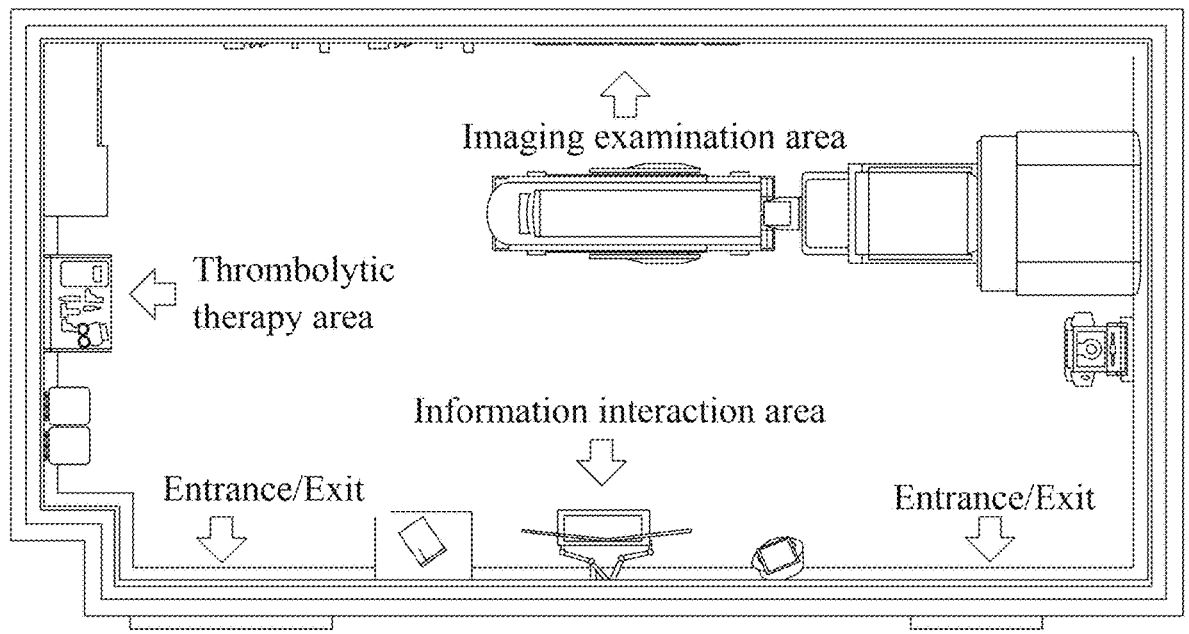
FIG. 1 is a schematic diagram of three-dimensional modeling of a regionally integrated emergency stroke unit according to the present disclosure.

Referring to FIG. 1, the present disclosure provides a regionally integrated emergency stroke unit (ESU), including: an information interaction area, an imaging examination area, a thrombolytic therapy area, and an entrance. A size of the regionally integrated emergency stroke unit may be 8.3 m×4 m.

Figure 2:
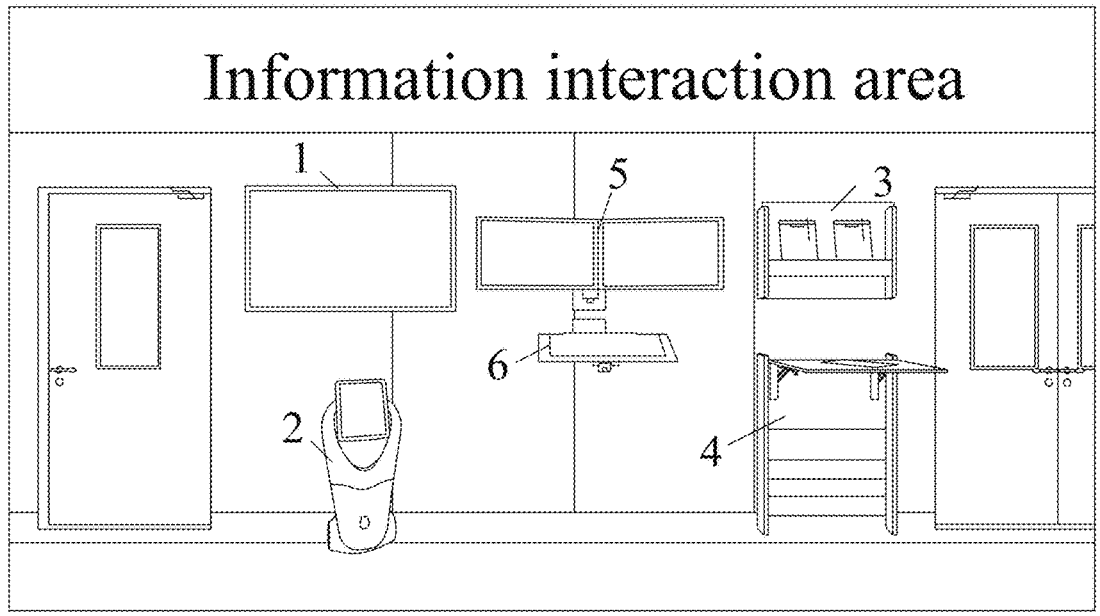
FIG. 2 is a schematic diagram of three-dimensional modeling of an information interaction area.

Referring to FIG. 2, a doctor workstation, a comprehensive information surveillance monitor 1, and a process support AI (artificial intelligence) assistant 2 are set in the information interaction area.

The doctor workstation includes a computer, a file rack 3, and a folding table 4. The computer includes a host, a dual-screen display 5, and a keyboard 6, and is configured for a doctor to enter and view information about a patient. In some embodiments, a size of a single display of the dual-screen display 5 may be 27 inches. The file rack 3 is configured to place a paper document. The folding table 4 may be a wall-mounted/wall-adhered folding table, and is configured to temporarily place and store a small medical device, an instrument, and a document. The symbol "/" used in the present disclosure means "and/or".

The comprehensive information surveillance monitor 1 is configured to display basic information, an arrival time at a hospital, an arrival time at a clinic, and vital signs of the patient, and a size may be 50 inches. The process support AI assistant 2 is configured to perform, via voice interaction or touchscreen keying interaction, automatic inquiry and auxiliary nervous system scale scoring, and further provide real-time retrieval support for a knowledge base and a clinical guideline.

Specifically, the process support AI assistant 2 is an AI intelligent robot. An intelligent interaction module is disposed in the process support AI assistant 2. An automatic inquiry function of the intelligent interaction module is to perform, based on an emergency structured record, structured questioning on key medical information about the patient such as a time of onset, an onset symptom, a concomitant symptom, a past medical history, and an allergy history, and perform voice recognition and enter an answer of the patient and/or a family of the patient, or enter, by the doctor, information provided by the patient and/or a family of the patient, and store the information as a structured consultation result. Subsequently, an AI-assisted decision-making system may provide suggestions for next diagnosis and therapy based on the consultation result in combination with an image.

A scoring function of the intelligent interaction module based on the auxiliary nervous system scale is to raise questions on each item of key auxiliary nervous system scales, for example, an NIHSS scale, an ABCD2 scale, and a pre-morbid mRS scale, perform voice recognition and enter an answer of the patient and/or the family of the patient, or enter, by the doctor, information provided by the patient and/or the family of the patient, thereby obtaining a scale score result. The NIHSS score is used to determine severity of a neurological deficit of the patient, and is an important basis for reperfusion therapy in an ischemic cerebrovascular disease (for example, cerebral infarction). The ABCD2 score is used to stratify a risk of cerebral infarction in a patient with transient cerebral ischemia, is an important reference for therapy such as antiplatelet aggregation, and helps assist the doctor in making a decision for next therapy. The pre-morbid mRS score is used to assess a pre-morbid functional status of the patient, and is an important basis for reperfusion therapy such as endovascular therapy for the ischemic cerebrovascular disease.

The retrieval support function of the intelligent interaction module is implemented via a large language model. The large language model includes a knowledge base related to clinical diagnosis and therapy of a stroke, including but is not limited to a clinical scale, an international/domestic guideline for acute cerebral infarction, a guideline for secondary prevention of cerebral infarction, a guideline for diagnosis and therapy of cerebral hemorrhage, a guideline for clinical diagnosis and therapy of subarachnoid hemorrhage. In a process of diagnosis and therapy, the doctor may directly ask a question with voice when retrieving corresponding information, and the intelligent interaction module gives feedback in real time. For example, when encountering a patient with cerebral infarction in an intravenous thrombolysis time window and with a suspected contraindication for thrombolysis, the doctor may ask the intelligent interaction module about an indication and a contraindication for alteplase intravenous thrombolysis, to quickly check whether the patient meets therapy indications and quickly assist in decision-making.

The process support AI assistant 2 is further configured to efficiently interact with medical staff, the patient and/or the family of the patient, and provide functions of explaining a medical process, illuminating a therapy regimen, and signing an informed consent form. The medical process and the therapy regimen include indications, contraindications, and possible risks and benefits of therapy such as reperfusion therapy (intravenous thrombolysis and intravascular thromboembolectomy), secondary prevention therapy (antiplatelet aggregation for the ischemic cerebrovascular disease, and lipid-lowering therapy). Problems about the therapy regimen concerned by the patient and families may help the doctor to provide corresponding data and recommend existing guidelines, and assist the doctor in explanation. When obtaining informed consent of the patient and the families, the doctor may remind the patient and the families of a signing position and mandatory content with voice, and assist in explaining current medical insurance policies of related drugs.

Figure 3:
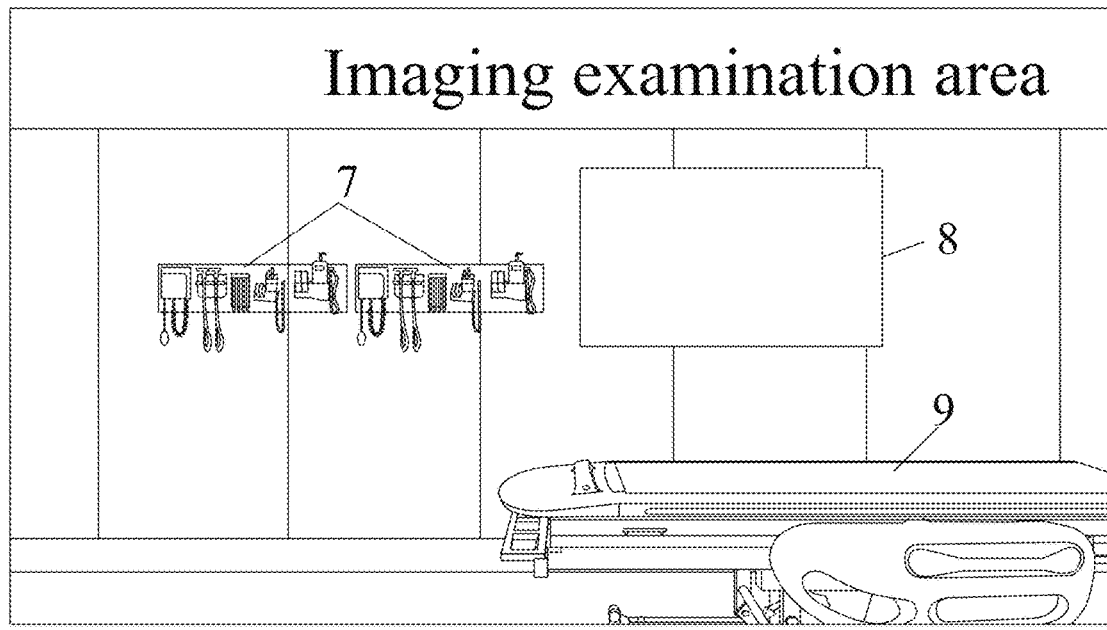
FIG. 3 is a schematic diagram of three-dimensional modeling of an imaging examination area.

Referring to FIG. 3, a test device 7, a first television display 8, a movable low-field magnetic resonance imager 9, and an AI-assisted decision-making system are set in the imaging examination area.

The test device 7 includes an electrocardiogramearable electrocardiogram monitor, a fingertip pulse oximeter, a sphygmomanometer, and a glucometer, and is configured to perform electrocardiogram, and monitor oxygen saturation, a blood pressure, and peripheral blood glucose of the patient. The test device further includes a non-invasive rapid genotyping tester for genes such as CYP2C19. The non-invasive rapid genotyping tester is configured to perform pharmacogenetic testing, to obtain a test result.

The first television display 8 is a large-sized television display with a size more than 60 inches, and is configured to amplify content on the comprehensive information surveillance monitor 1 in the information interaction area for display.

The movable low-field magnetic resonance imager is set in the imaging examination area, and is configured to perform nuclear magnetic scanning on the patient, to generate MRI results of a head and neck of the patient. The movable low-field magnetic resonance imager in the present disclosure is a movable low-field (0.23 T) MRI device that has no magnetic shielding requirements and that is easy to use, and is configured to perform rapid imaging assessment for the patient with the acute stroke, identify cerebral infarction and cerebral hemorrhage within 10 minutes, and assess great vessels. Therefore, problems, for example, a MRI system of the head and neck has a small aperture, incidence of claustrophobia is relatively high, and a patient with macrosomia cannot complete the MRI examination, are resolved. Further, shortcomings of high-field MRI, for example, accessibility is poor, scanning time is long, high-field MRI cannot be applied to neuroimaging assessment of the acute stroke, are made up. In addition, a bottleneck that the stroke patient undergoes cranial computed tomography (CT) in a separate CT room is broken through. This improves diagnostic accuracy of the patient and greatly shortens a time from arrival to therapy.

A movable MRI system is integrated into the movable low-field magnetic resonance imager 9 in the present disclosure. The movable MRI system uses an artificial intelligence image analysis technology. Therefore, a detection time is significantly shortened, and image quality is improved. This assists the doctor in identifying ischemia/ hemorrhage, identifying an infarct core site and volume, identifying large artery occlusion/stenosis, and determining duration of onset of a patient with a wake-up stroke, thereby quickly making decisions for therapy. Specifically, the movable MRI system implements, based on a large number of low-field and high-field MRI datasets of a same patient, image super-resolution reconstruction by developing an image reconstruction method based on deep learning. This greatly improves details and contrast of a 0.23 T MRI image, improves image quality, and shortens a scanning time.

The AI-assisted decision-making system is in communication connection with the comprehensive information surveillance monitor 1, the process support AI assistant 2, the test device 7, the first television display 8, and the movable low-field magnetic resonance imager 9 separately. The AI-assisted decision-making system is configured to assist in decision-making based on an automatic inquiry result, a scale score result, the test result, and MRI results of the head and neck, to generate and display a therapy regimen.

The AI-assisted decision-making system is configured to quickly and accurately recognize a site of acute cerebral infarction by developing a deep learning method based on a large number of manually labeled datasets, and automatically calculate an infarct volume. The AI-assisted decision-making system is further configured to determine, based on a magnetic resonance angiography (MRA) sequence of movable magnetic resonance, whether the patient exhibits intracranial large artery occlusion/stenosis. The AI-assisted decision-making system is further configured to align a different sequence (DWI/FLAIR) to standard space using an automatic alignment technique, to implement automatic recognition on a diffusion-weighted imaging-fluid attenuated inversion recovery (DWI/FLAIR) mismatch of the site of acute cerebral infarction, determine an approximate time of onset of wake-up stroke, and guide reperfusion therapy. The AI-assisted decision-making system is further configured to determine, based on image interpretation information and a total of NIHSS scores obtained by the intelligent interaction module, whether the patient has a clinical-imaging mismatch, and assist, in combination with the infarct volume, in determining whether endovascular therapy needs to be conducted for the patient to implement intracranial reperfusion.

Figure 4:
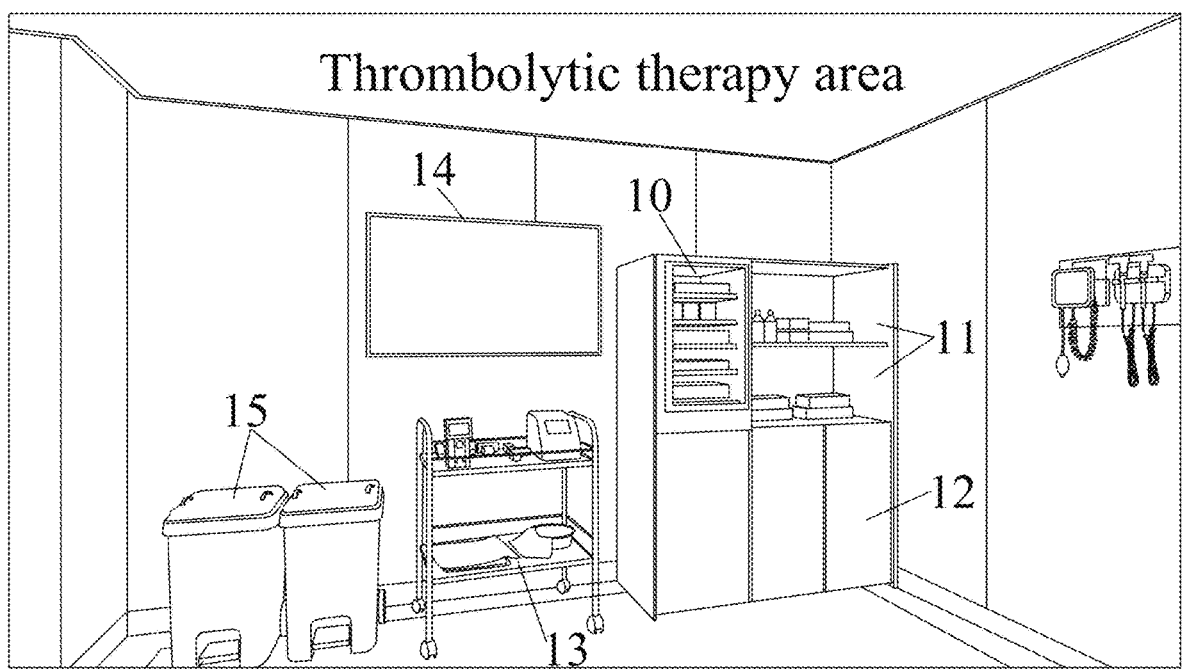
FIG. 4 is a schematic diagram of three-dimensional modeling of a thrombolytic therapy area.

Referring to FIG. 4, a small refrigerator 10, a first aid medicine cabinet 11, and a storage cabinet 12 are set in the thrombolytic therapy area, and configured to store medicines, reagents, and first aid medicines with different temperature requirements. A temperature display and setting device is set in the small refrigerator 10, and configured to monitor a storage temperature of the medicines in real time. A size of the small refrigerator 10 may be designed as 0.5 m×0.5 m×0.8 m. A size of the first aid medicine cabinet 11 may be designed as 1.4 m×0.6 m×1.7 m. For example, teneplase needs to be stored under 25° C. and protected from light, and used immediately after being dissolved. If teneplase is not used immediately, teneplase needs to be refrigerated at 2° C. to 8° C. and protected from light, and used within 24 h. Alteplase needs to be stored under 25° C. and protected from light, and used immediately after being dissolved. If alteplase is not used immediately, alteplase needs to be refrigerated at 2° C. to 8° C. and protected from light, and used within 24 h.

A small ambulance 13 is further set in the thrombolytic therapy area, and is configured to rescue the patient in a medical emergency. A size of the small ambulance 13 may be designed as 0.7 m×0.5 m×1.5 m. Items stored in the small ambulance 13 are shown in FIG. 5, and stored medicines need to be sealed under 20° C. and protected from light. A 42-inch second television display 14 is further set in the thrombolytic therapy area, and configured to display content on the comprehensive information surveillance monitor 1 in the information interaction area. Medical and household trash cans 15 are further set in the thrombolytic therapy area, and configured to temporarily place medical garbage or household garbage. A size of the trash can 15 may be designed as 0.45 m×0.3 m×0.3 m. A vital signs monitoring system, for example, an electrocardiogram monitor and a blood pressure monitor, and a genetic test device are further set in the thrombolytic therapy area. Corresponding parameters may be displayed on the television display/monitor in the respective area. A camera is further installed in the thrombolytic therapy area, and is configured to implement online interconnection and remote monitoring functions between the doctor and the patient in combination with the second television display.

A new generation of thrombolytic drugs and other necessary medicines are placed in the thrombolytic therapy area. A medication regimen is quickly determined by pharmacogenetic testing. Based on the non-invasive rapid genotyping tester based on drug metabolism genes such as CYP2C19, the doctor or a nurse collects cells exfoliated from mouth mucosa of the patient using a mouth swab, to test genotyping of genes such as CYP2C19 (a key gene for clopidogrel metabolism), CYP2C9 (a key gene for warfarin metabolism), and VKORC (a key gene for warfarin metabolism). Results are automatically transmitted to the AI-assisted decision-making system, effectiveness and safety of various types of drugs for the patient are preliminary determined based on the genotyping of the key gene for drug metabolism, and therapy suggestions are given. For example, for a patient who carries the CYP2C19 *2 or *3 allelic gene and needs to be treated with double antiplatelet aggregation therapy, clopidogrel metabolism may be medium or slow metabolism, affecting effectiveness. Clopidogrel may be replaced with tegretol in the absence of contraindications.

The regionally integrated emergency stroke unit in the present disclosure is a unique integrated unit for therapy of the acute stroke, highly concentrates traditional organizational management for the acute stroke in a room, and incorporates an innovative solution, to form three areas, namely, the information interaction area, the imaging examination area, and the thrombolytic therapy area. Therefore, it is expected to compress the time from arrival to the reperfusion therapy of the patient to less than 20 minutes, and assist the medical staff, the patient, and the family in obtaining high-quality diagnosis and therapy experience. After arriving at the hospital, the patient first enters the imaging examination area of the regionally integrated ESU. The intelligent wearable device is set in the imaging examination area, to collect key information such as the vital signs of the patient in real time. The movable low-field magnetic resonance imager in the imaging and examination area has a small volume, a light weight, low requirements for a metal implant in the patient, a simple magnetic resonance operation interface, package-type scanning setup, and low requirements for a field, and is removable, safer, and easy to grasp. Therefore, the patient does need to travel between a consultation room, a scanning room, a laboratory room, and a therapy room. This is superior to a traditional CT examination solution. The AI-assisted decision-making system includes an innovative identification sequence. Therefore, cerebral hemorrhage and cerebral ischemia can be quickly identified within one and a half minutes, to conduct reperfusion therapy in the patient with the acute ischemic stroke within the shortest time, thereby improving brain function, reducing a disability rate, and improving long-term survival quality. A resolution of the brain image can be further improved through a high-definition processing technology of an AI image. Therefore, the resolution of the brain image rivals that of a high-field nuclear magnetic image. The information interaction area uses an integrated information system, to quickly enter fully-structured data, implement AI-assisted decision-making based on signs and imaging manifestations, and display key data in real time throughout the whole process, thereby helping medical teams to quickly make decisions. An AI intelligent robot is further set in the information interaction area, to provide functions such as explaining the medical process, explaining the therapy regimen, and signing the informed consent form. This helps the medical staff to improve communication efficiency. The thrombolytic therapy area can support online interconnection and remote monitoring between the doctor and the patient, and is equipped with a new generation of thrombolytic drugs and advanced thrombolytic devices. The antiplatelet therapy regimen may be quickly determined via a genetic test device bedside a sickbed, to maximize the clinical benefits for the patient.

The regionally integrated emergency stroke unit in the present disclosure quickly enters the fully structured information/data via the intelligent interaction module, implements AI-assisted decision-making based on the signs and the imaging manifestations via the AI-assisted decision-making system, and displays key medical data in real time throughout the whole process via the television display/monitor in each area. The key medical data can be automatically collected and updated by seamlessly connecting the AI-assisted decision-making system to the medical device, to reflect conditions of the patient in real time. The key medical data include test results from wearable devices or point-of-care (POC) test devices such as an electrocardiogra glucometer, a sphygmomanometer, and a non-invasive rapid genotyping tester such as CYP2C19. The doctor or the nurse connects chest lead electrodes and limb lead electrodes for the patient to take an electrocardiogram. The doctor or the nurse takes peripheral blood from the patient to rapidly test blood sugar levels. The doctor or the nurse ties cuffs for the patient to collect a blood pressure value. The doctor or the nurse collects the cells exfoliated from mouth mucosa of the patient, to conduct rapid genotyping testing of genes such as CYP2C19.

The fully structured information/data is collected based on structured questioning (choice questions) for the test device and the intelligent interaction module, including: test results from the wearable devices or the POC test devices such the electrocardiogramapid glucometer, the sphygmomanometer, and the non-invasive rapid genotyping tester such as CYP2C19; and symptoms of the patient (weakness in limbs, inarticulate speech, and blurred vision), signs (whether muscle strength is reduced, whether there is a defect of a field vision, whether there is dysarthrosis, and whether there is aphasia), and a past history (whether having a hypertension history and a diabetes history). The doctor collects a medical history of the patient via the intelligent interaction module, enters content narrated by the patient with voice during a physical examination and collection of the signs, and quickly enters the fully structured information/data.

The signs are information obtained during the physical examination. The imaging manifestations include information on the presence of an intracranial ischemic lesion, the presence of an intracranial hemorrhagic lesion, the presence of a DWI/FLAIR imaging mismatch, and the presence of intracranial large artery occlusion. Etiological typing is automatically conducted for the clinical diagnosis and therapy of the cerebrovascular disease via the AI-assisted decision-making system, and recommendations for next examinations and therapy are given, to assist the doctor in decision-making.

In the present disclosure, a holistic medical AI-assisted decision-making system is constructed using the artificial intelligence technology. Therefore, the doctor can obtain analysis results within a few minutes and quickly determine a therapy regimen. The analysis results include: primary diagnosis (based on the symptoms, the signs, and the imaging manifestations) of the patient, etiological typing (based on the signs, the past history, and the imaging manifestations), the presence of an imaging mismatch (based on the imaging manifestations), the presence of a clinical-imaging mismatch (based on the signs, the scale scores, and the imaging manifestations), and the presence of intracranial large artery occlusion (based on the imaging manifestations).

The AI-assisted decision-making system is further configured for clinical diagnosis and therapy of the acute cerebrovascular disease, especially configured to recommend therapy suggestions based on matching of indications and contraindications for reperfusion therapy.

The AI-assisted decision-making system may be further configured to automatically remind the doctor to immediately treat, with rtPA or TNK, a patient who meets thrombolysis indications, and continuously monitor the vital signs, remind the doctor to immediately enter an informed consent process for a patient who meets indications for intravenous thrombolytic therapy, after obtaining the informed consent of the patient and the family, immediately conduct intravenous thrombolytic therapy under vital signs monitoring, and remind the doctor to immediately explain an endovascular therapy rescue process for a patient who meets indications for endovascular therapy. In addition, a duty doctor in the interventional department is immediately called via the intelligent interaction module. After arrival, the duty doctor assists the doctor in obtaining the informed consent of the patient and the family, and transfers the patient to a catheterization room for endovascular therapy.

In the present disclosure, the emergency room, the laboratory room, the imaging examination room, and a pharmacy are innovatively integrated into a single room, and concept of integration of the acute stroke unit is proposed. Diagnosis and therapy routes for the patient with the acute ischemic stroke are highly centralized by integrating the information interaction area, the imaging examination area, and the thrombolytic therapy area. Therefore, after the patient with the ischemic stroke arrives at the hospital, the delay of the patient is minimized. Certainly, in practical application, the regional integration of the acute stroke unit can be expanded or reduced as required.

In the regionally integrated emergency stroke unit provided in the present disclosure, three areas, namely, the information interaction area, the imaging examination area, and the thrombolytic therapy area are integrated, integrating functions such as real-time vital signs monitoring, intelligent consultation, neurological specialty examination scoring, movable MRI, and rapid pharmacogenetic testing, and an innovative and optimized in-hospital diagnosis and therapy system for the acute ischemic stroke is created. Specifically, concept of integration of an acute stroke unit is applied to the ESU in the present disclosure, integrating all aspects such as triage, consultation, physical examinations, laboratory tests, examinations, development for diagnosis and therapy regimens, and therapy for the patient with the acute ischemic stroke. Therefore, after arrival at an emergency clinic, a movement range of the patient is greatly reduced in a patient-centered manner. After entering the ESU, a suspected patient with the acute stroke first arrives in the information interaction area, and the process support AI assistant 2 conducts information entry, questioning, neurological examinations, and scale evaluation. Then, the patient arrives in the imaging examination area, the doctor or the nurse completes the electrocardiogram, measurement of the blood pressure, the oxygen saturation, and the peripheral blood glucose. Relevant information is entered into the process support AI assistant 2 in the information interaction area with voice or touchscreen, and displayed on the television display/monitor in each area. After determining that the patient has no contraindications to movable low-field magnetic resonance scanning, the doctor conducts movable low-field magnetic resonance scanning for the patient, reads a film in real time during scanning, and preliminarily determines the disease. The doctor gives preliminary informed consent for intravenous thrombolytic therapy to a legal representative (the family member) of the patient who meets indications for intravenous thrombolytic therapy. If the patient is clear in consciousness, after the scan is completed, the doctor introduces risks and benefits of intravenous thrombolytic therapy to the patient, and obtains informed consent. If the patient or the legal representative of the patient signs the informed consent for intravenous thrombolysis, the patient is placed on a therapy bed (provided when the patient is examined, and provided when the patient enters on foot or in a wheelchair), and parked in the thrombolytic therapy area for intravenous thrombolytic therapy under electrocardiogra pressure, and clinical monitoring. A patient who does not meet the indications for intravenous thrombolytic therapy or who refuses intravenous thrombolytic therapy enters a routine diagnosis and therapy process. Images and reports of the movable low-field magnetic resonance imager may be queried in a medical picture archiving and communication (PACS) system.

Diagnostic accuracy and a diagnostic speed of the doctor are improved via the AI-assisted decision-making system used in the present disclosure, and this provides a solution for quickly developing a precise therapy regimen. Due to the movable MRI system, a detection time can be greatly shortened using an artificial intelligence image analysis technology. In addition, image quality is improved. This assists the doctor in identifying the ischemia/hemorrhage, identifying the core infarct site and volume, identifying the large artery occlusion/stenosis, and determining the duration of the onset of the patient with the wake-up stroke, thereby quickly making decisions for therapy. Regional integration of a whole process of examinations, thrombolysis, and further therapy for the patient with the ischemic stroke by integrating independent operation units. Therefore, after the patient with the ischemic stroke arrives at the hospital, the delay of the patient is minimized. When thrombi are lysed or removed early and reperfusion therapy is conducted for brain tissues in an ischemic region, more brain tissues can be salvaged and clinical prognosis is improved, which has promising application prospects.

Particular examples are used herein for illustration of principles and implementation modes of the present disclosure. The descriptions of the above embodiments are merely used for assisting in understanding the method of the present disclosure and its core ideas. In addition, those of ordinary skill in the art can make various modifications in terms of particular implementation modes and the scope of application in accordance with the ideas of the present disclosure. In conclusion, the content of the description shall not be construed as limitations to the present disclosure.

What is claimed is:

1. A regionally integrated emergency stroke unit, comprising: an information interaction area, an imaging examination area, and a thrombolytic therapy area, wherein
   a doctor workstation, a comprehensive information surveillance monitor, and a process support artificial intelligence (AI) assistant are set in the information interaction area; the doctor workstation comprises a computer, a file rack, and a folding table; the computer is configured for a doctor to enter information; the file rack is configured to place a document; the folding table is configured to temporarily place and store a medical device and a document; the comprehensive information surveillance monitor is configured to display basic information, an arrival time at a hospital, an arrival time at a clinic, and vital signs of a patient; and the process support AI assistant is configured to perform, via voice interaction or touchscreen keying interaction, automatic inquiry and auxiliary nervous system scale scoring, and further provide real-time retrieval support for a knowledge base and a clinical guideline;
   an intelligent interaction module is disposed in the process support AI assistant; and the intelligent interaction module is configured to perform, based on an emergency structured record, structured questioning on key medical information about the patient comprising a time of onset, an onset symptom, a concomitant symptom, a past medical history, and an allergy history, perform voice recognition on an answer of the patient and/or a family of the patient, and perform structured entry of the key medical information;
   the intelligent interaction module is further configured to score via voice interaction or touchscreen keying interaction with the patient and/or the family of the patient based on the auxiliary nervous system scale comprising a National Institute of Health stroke scale (NIHSS), an age, blood pressure, clinical features, duration, diabetes (ABCD2) scale, and a pre-morbid modified rankin scale (mRS), to obtain a scale score result;
   a large language model is further stored in the intelligent interaction module; the large language model comprises a knowledge base related to clinical diagnosis and therapy of a stroke, comprising a clinical scale, a guideline for acute cerebral infarction, a guideline for secondary prevention of cerebral infarction, a guideline for diagnosis and therapy of cerebral hemorrhage, a guideline for clinical diagnosis and therapy of subarachnoid hemorrhage; and in a process of diagnosis and therapy, retrieval of the knowledge base and the clinical guideline is implemented via voice interaction or touchscreen keying interaction with the doctor;
   a test device, a first television display, a movable low-field magnetic resonance imager, and an AI-assisted decision-making system are set in the imaging examination area; the test device is configured to perform electrocardiogram examination and pharmacogenetic testing, and monitor oxygen saturation, a blood pressure, and peripheral blood glucose of the patient, to obtain a test result; the first television display is configured to amplify content on the comprehensive information surveillance monitor for display; the movable low-field magnetic resonance imager is configured to perform magnetic resonance imaging (MRI) on a head and neck of the patient; the AI-assisted decision-making system is in communication connection with the comprehensive information surveillance monitor, the process support AI assistant, the test device, the first television display, and the movable low-field magnetic resonance imager separately; and the AI-assisted decision-making system is configured to assist in decision-making based on an automatic inquiry result, the scale score result, the test result, and MRI results of the head and neck, to generate and display a therapy regimen; and a small refrigerator, a first aid medicine cabinet, and a storage cabinet are set in the thrombolytic therapy area, and configured to store medicines, reagents, and first aid medicines with different temperature requirements; an ambulance and a vital signs monitoring system are further set in the thrombolytic therapy area; the ambulance is configured to rescue the patient in medical emergency; and the vital signs monitoring system is configured to monitor and display the vital signs of the patient in real time;

wherein new-generation thrombolytic drugs and necessary medicines are provided in the thrombolytic therapy area, and a medication regimen is determined by pharmacogenetic testing; genotyping of genes of CYP2C19, CYP2C9, and VKORC are determined by a non-invasive rapid genotyping tester; and results are automatically transmitted to the AI-assisted decision-making system, effectiveness and safety of various types of drugs for the patient are preliminary determined based on genotyping of key genes for drug metabolism, and therapy suggestions are given.

2. The regionally integrated emergency stroke unit according to claim 1, wherein the intelligent interaction module is further configured to provide, via voice interaction or touchscreen keying interaction with the patient and/or the family of the patient, functions of explaining a medical process, illuminating a therapy regimen, and signing an informed consent form.

3. The regionally integrated emergency stroke unit according to claim 1, wherein the test device comprises an electrocardiogramarable electrocardiogram monitor, a fingertip pulse oximeter, a sphygmomanometer, a glucometer, and a non-invasive rapid genotyping tester.

4. The regionally integrated emergency stroke unit according to claim 1, wherein a movable MRI system is integrated inside the movable low-field magnetic resonance imager; and the movable MRI system implements, based on low-field and high-field MRI datasets of the patient, image super-resolution reconstruction through an image reconstruction method based on deep learning, to obtain the MRI results of the head and neck.

5. The regionally integrated emergency stroke unit according to claim 4, wherein the AI-assisted decision-making system is configured to recognize a site of acute cerebral infarction from the MRI results of the head and neck through a deep learning method, and automatically calculate an infarct volume; the AI-assisted decision-making system is further configured to determine, based on a magnetic resonance angiography (MRA) sequence of movable magnetic resonance, whether the patient exhibits intracranial large artery occlusion/stenosis; and the AI-assisted decision-making system is further configured to align a different sequence to standard space using an automatic alignment technique, to implement automatic recognition on a diffusion-weighted imaging-fluid attenuated inversion recovery (DWI/FLAIR) mismatch of the site of acute cerebral infarction, determine an approximate time of onset of wake-up stroke, and guide reperfusion therapy.

6. The regionally integrated emergency stroke unit according to claim 5, wherein the AI-assisted decision-making system is further configured to determine, based on image interpretation information and the scale score result, whether the patient has a clinical-imaging mismatch, and assist, in combination with the infarct volume, in determining whether endovascular therapy is required to be conducted for the patient to implement intracranial reperfusion.

7. The regionally integrated emergency stroke unit according to claim 1, wherein a second television display and a trash can are further set in the thrombolytic therapy area; the second television display is configured to display content on the comprehensive information surveillance monitor; and the trash can is configured to temporarily place medical garbage or household garbage.

* * * * *